(12) United States Patent
Kobarfard et al.

(10) Patent No.: US 6,482,982 B1
(45) Date of Patent: Nov. 19, 2002

(54) HALOGENATED ANTITUBERCULOSIS AGENTS

(75) Inventors: Farzad Kobarfard, Philadelphia; Joel M. Kauffman, Wayne, both of PA (US)

(73) Assignee: University of Sciences of Philadelphia, Philadelphia, PA (US)

(*) Notice: Subject to any disclaimer, the term of this patent is extended or adjusted under 35 U.S.C. 154(b) by 0 days.

(21) Appl. No.: 09/803,006

(22) Filed: Mar. 8, 2001

(51) Int. Cl.$^7$ .................. C07C 337/06; C07C 281/06
(52) U.S. Cl. ........................... 564/18; 564/34
(58) Field of Search ...................... 564/18, 34

(56) References Cited

U.S. PATENT DOCUMENTS 4,962,111 A  10/1990  Welch et al. ............... 514/255

OTHER PUBLICATIONS

CA:51:63597 abs of Kekkaku by Nakaguchi 32 pp 31–5 1957.*
CA:125:184913 abs of Arzneim Forsch by Saripinar et al 46(8) pp 824–828.*
Chemical abstracts vol. 52 abstract 17509d by Gheorghiu.*
Evans, Jon: Chemistry in Britain, Nov. 1998 pp 38–41.

* cited by examiner

*Primary Examiner*—Jean F. Vollano
(74) *Attorney, Agent, or Firm*—RatnerPrestia

(57) ABSTRACT

Halogenated derivatives of two synthetic anti-tuberculosis agents, thioacetazone and p-aminosalicylic acid, have been synthesized. In general, the halogenated compound has the structure of Structure I:

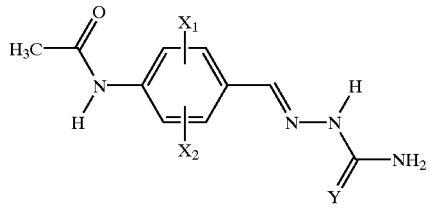

Structure I wherein $X_1$ is a halogen and $X_2$ is a second halogen or hydrogen, and Y is sulfur or oxygen; or, has the structure of Structure IV:

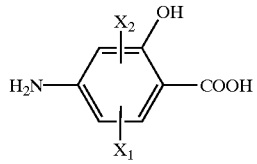

Structure IV wherein $X_1$ is a halogen and $X_2$ is a second halogen or hydrogen. Alternatively, the halogenated compounds may be pharmaceutically acceptable salts of these compounds. These halogenated derivatives possess anti-mycobacterial activity and are particularly useful for the treatment of Mycobacterium tuberculosis infections. In particular, fluorinated analogs of thioacetazone and p-amino-salicylic acid have been synthesized for use as anti-tuberculosis therapeutic agents either alone or in combination with other conventional anti-tuberculosis therapeutic agents.

21 Claims, No Drawings

HALOGENATED ANTITUBERCULOSIS AGENTS

BACKGROUND OF THE INVENTION

1. Field of the Invention

This invention relates generally to the field of therapeutic agents that have anti-mycobacterial activity. More particularly, this invention relates to halogenated compounds that have anti-mycobacterium tuberculosis activity, therapeutic agents for treating tuberculosis and methods of treating tuberculosis.

2. Description of Related Art

Tuberculosis is the oldest documented infectious disease, and it remains an important global health problem. An estimated I billion people worldwide are infected with *Mycobacterium tuberculosis;* 8 to 10 million new tuberculosis cases occur each year, and the number of new cases is estimated to increase to 12 million in the year 2005. Inadequacy of diagnosis and prevention in addition to inefficient treatment programs account for uncontrolled infection in developing countries.

Therapies exist to treat tuberculosis, however tuberculosis is not entirely cured by present drug treatments. Current drugs can minimize relapse rates with optimal treatment. With the best available chemotherapy, tubercle bacilli are slowly disposed of or killed. The widespread use of some drugs, such as isoniazid, has resulted in the development of resistant strains such that current drugs fail to eradicate some Mycobacterial infections. Therefore new drugs with anti-mycobacterial action are essential to successfully treat tuberculosis infections.

Because Mycobacteria develop resistance to drugs, optimal anti-tuberculous therapies require the use of several drugs in combination. Mycobacterial populations contain spontaneous mutants that are resistant to drugs even prior to exposure. The frequency of such mutations can vary between 1 in less than 100 to 1 in greater than 10,000, depending upon the drug. Single drug therapy can inhibit the majority of organisms in an infected site, yet permit, and in fact encourage, uncontrolled growth of the resistant mutants. Early combination therapy with at least two drugs is the preferred method of preventing emergence of large resistant populations in the original tuberculous cavities. Some drugs are most valuable for their ability to suppress emergence of resistance during combination therapy. An example is p-aminosalicylic acid, which can delay development of streptomycin resistance.

Thus, anti-mycobacterial agents can be important not only for their own efficacy against susceptible organisms but for their ability to enhance effectiveness of other agents by controlling emergence of resistant populations, for example populations resistant to pyrazinamide. Pyrazinamide is a major drug used in the therapy of tuberculosis and the synthesis of pyrazinamide was described by Kushner et al, J. Am. Chem. Soc. 74:3617 (1952), and the compound was patented in 1954 as a tuberculostatic agent (U.S. Pat. No. 2,677,641 issued to Williams). When pyrazinamide is used alone resistance develops quickly, and for this reason it is usually administered in combination with other drugs such as isoniazid. Pyrazinamide is also hepatotoxic, which further limits its use as a therapeutic agent.

The development of new anti-mycobacterial agents presents a challenge of balancing toxicity to mycobateria with patient safety. Due to fluorine's unique chemistry, fluorinated compounds offer some desirable features in pharmacological applications. For example, fluorine is the second smallest element, after hydrogen, and thus, fluorine closely mimics hydrogen at enzyme receptor sites. Fluorine's high electronegativity typically alters chemical reactivity at these enzyme sites, and enzyme deactivation can result. However, high electronegativity also increases oxidative and thermal stability as a C—F bond is stronger than a C—H bond, which can also affect enzymatic activity. In some cases (e.g., 5-fluorouracil), the specific location of a "deceptor" fluorine instead of hydrogen blocks, an essential biochemical reaction. The presence of fluorine may also promote lipid solubility, thereby enhancing drug absorption and transport rates in vivo.

Fluorinated organic molecules can be effective in the treatment of a variety of disorders. However, fluorination of compounds for the treatment of *M. tuberculosis* has not previously been successful. Isoniazid is one of the most active drugs for the treatment of tuberculosis. Fluorination of the pyridine ring of isoniazid resulted in drastically decreasing activity against *M. tuberculosis.*

The global resurgence of tuberculosis and development of drug resistant populations have rekindled the need for and interest in the development of new anti-tubercular drugs. However no new anti-tuberculosis agents have been developed since the introduction of rifampin into clinical use. There continues to be a need for new compounds with high efficacy in anti-tuberculosis activity for use as therapeutic agents.

SUMMARY OF THE INVENTION

These needs are met by the halogenated compounds of this invention, which possess high anti-tuberculosis activity or are useful as intermediates in the manufacture of such compounds.

In one embodiment of this invention, a class of compounds which possess high anti-tuberculosis activity includes:

a halogenated compound having Structure I or a pharmaceutically acceptable salt thereof:

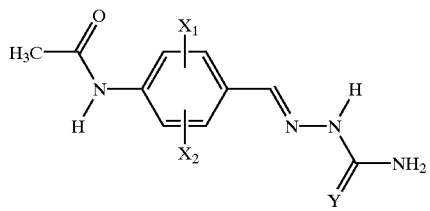

Structure I wherein $X_1$ is a halogen and $X_2$ is a second halogen or hydrogen, and Y is sulfur or oxygen; and, a halogenated compound having Structure II:

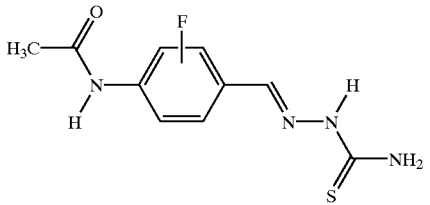

Structure II or a pharmaceutically acceptable salt thereof.

In another embodiment of this invention, a class of compounds which possess high anti-tuberculosis activity includes: a halogenated compound having Structure IV or a pharmaceutically acceptable salt thereof:

Structure IV

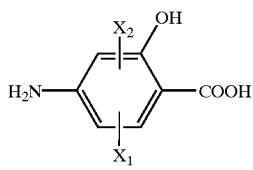

wherein $X_1$ is a halogen and $X_2$ is a second halogen or hydrogen; a halogenated compound having Structure V or pharmaceutically acceptable salt thereof:

Structure V

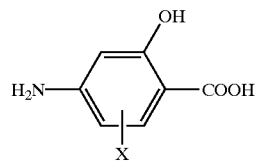

wherein X is a halogen; and a halogenated compound having Structure VI:

Structure VI

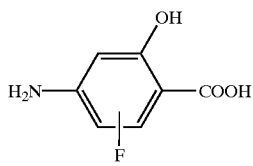

or a pharmaceutically acceptable salt thereof.

A further embodiment of this invention, is a composition, which possess high anti-tuberculosis activity comprising any one of the halogenated compounds of this invention and a pharmaceutically acceptable binder, wherein the halogenated compound has anti-mycobacterium activity.

A still further embodiment of this invention is a method of treating a mammal infected with a Mycobacterium, comprising administering to the mammal a non-toxic, effective amount of a composition comprising any one of the halogenated compounds of this invention and a pharmaceutically acceptable binder, wherein the halogenated compound has anti-mycobacterium activity.

A still further embodiment of this invention is a halogenated compound having Structure III:

Structure III

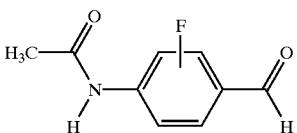

wherein the compound of Structure III is useful as an intermediate in the manufacture of compounds of Structure II.

DETAILED DESCRIPTION OF THE INVENTION

The novel halogenated compounds of this invention which are halogenated derivatives of two synthetic anti-tuberculosis agents, thioacetazone and p-aminosalicylic acid, have been synthesized. Halogenation (noted by $X_1$ or $X_2$) may be at any unsubstituted ring position in the structure. In general, the halogenated compound of this invention has the structure of Structure I:

Structure I

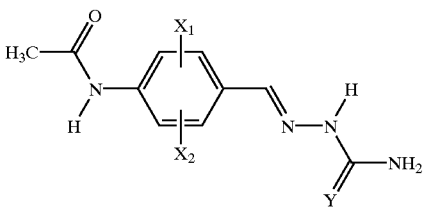

wherein Xi is a halogen and $X_2$ is a second halogen or hydrogen, and Y is sulfur or oxygen; or, has the structure of Structure IV:

Structure IV

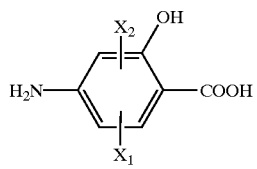

wherein $X_1$ is a halogen and $X_2$ is a second halogen or hydrogen. Alternatively, compounds of this invention may be pharmaceutically acceptable salts of compounds having Structures I and/or IV. Typical pharmaceutically acceptable salts include hydrochloride salts, hydrobromide salts, sulfate salts, and the like. The halogenated derivatives of Structures I and IV possess anti-mycobacterial activity and are particularly useful for the treatment of tuberculosis. In particular, fluorinated, chlorinated, brominated and iodinated analogs of thioacetazone and fluorinated analogs of p-aminosalicylic acid have been synthesized for use as anti-tuberculosis therapeutic agents either alone or in combination with other conventional anti-tuberculosis theraputic agents.

Conventional Thioacetazone During the screening of intermediates from the synthesis of sulfathiadiazoles, benzaldehyde thiosemicarbazone was shown to be active against tuberculosis. Structural modification produced the 4-acetamido derivative, thioacetazone.

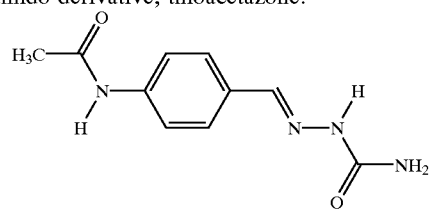

Thiacetazone

The mechanism of action is not known. Studies have shown that the thiosemicarbazones are not competitive inhibitors of p-aminobenzoic acid, and there is no cross-resistance with isoniazid.

Replacement of the thiosemicarbazone group with a semicarbazone, hydrazone, or oxime yields inactive compounds. Substitution on the primary amines of the thiosemicarbazone group with one or two alkyl groups or the sulfur atom with oxygen or nitrogen results in loss of activity. The order of activity of p- substitutions is:

Synthesis of fluorinated analog of Thioacetazone.

The fluoro derivative of thioacetazone was synthesized using the following reactions. In the following synthesis schemes and examples major reactants and products are identified with a bold face number; and the acronyms ACN, Ac, and Et have their conventional meaning, i.e., respectively acrylonitrile, acetic, and ethyl. 4-Acetamido-3-fluorobenzaldehyde 15 was synthesized from 4-acetamidobenzaldehyde 14 through a reaction with Selectfluor™ fluorinating agent (Aldrich #43,947-9,[1-(chloromethyl)-4-fluoro-1, 4-diazoniabicyclo[2.2.2]octane bis(tetrafluoro-borate)]).

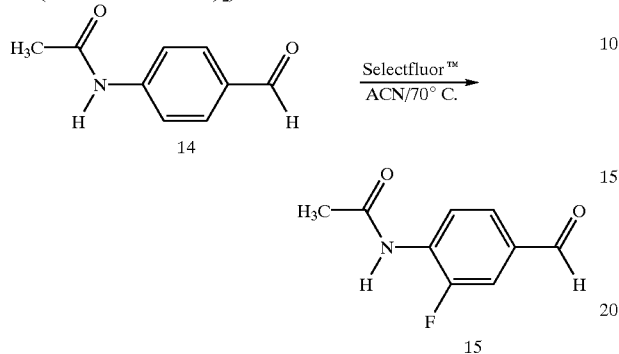

14
15

Synthesis of 4-acetamido-3-fluorobenzaldehyde 15

The product was characterized as 4-acetamido-3-fluorobenzaldehyde 15. 4-Acetamido-3-fluorobenzaldehyde 15 reacts with thiosemicarbazide to yield 4-acetamido-3-fluorobenzaldehyde thiosemicarbazone 16. Compound 16 has been tested and shown to be both non-toxic and highly active against *M. Tuberculosis.*

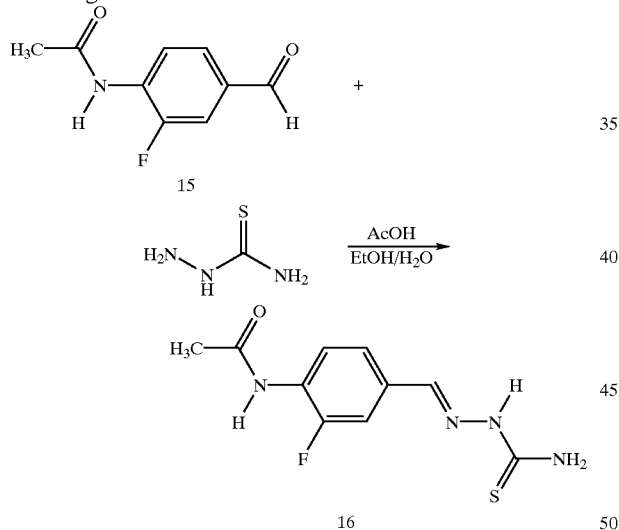

15
16

Synthesis of 4-acetamido-3-fluorobenzaldehyde thiosemicarbazone (16)

Synthesis of other halogenated analogs of thioacetazone

Synthesis of a positional isomer of compound 16, 4-acetamido-2-fluorobenzaldehyde thiosemicarbazone 17, and other halogenated analogs of thiacetazone are also described herein, as halogenated compounds of the present invention.

2-Fluoro derivative of Thiacetazone

The 2-fluoro positional isomer may be synthesized through several approaches. In one approach, 4-acetamido-2-fluorobenzaldehyde thiosemicarbazone 17 is prepared using the following approach. 4-Cyano-3-fluoroacetanilide 21 is first prepared in the following reaction scheme:

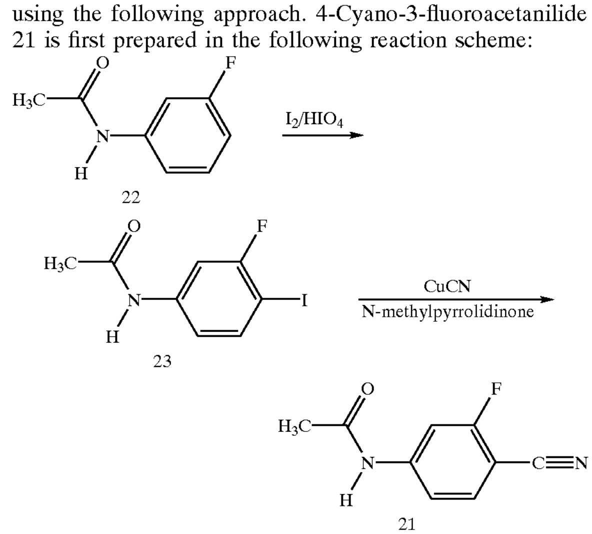

22
23
21

Preparation of 4-acetamido-2-fluorobenzonitrile 21 in which 3-fluoroacetanilide 22 is converted to 4-cyano-3-fluoroacetanilide 21. 4-Acetamido-2-fluorobenzaldehyde 20 is next synthesized by reducing the nitrile derivative, 4-cyano-3-fluoroacetanilide 21, with Raney nickel, as illustrated below.

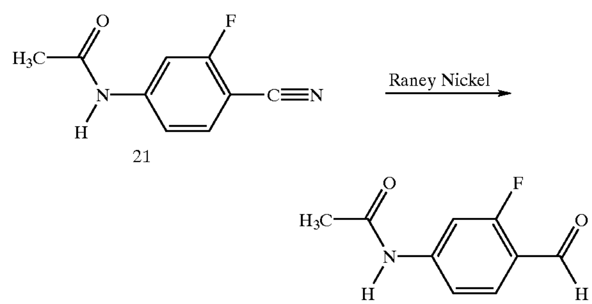

21
20

Synthesis of 4-acetamido-2-fluorobenzaldehyde 20

4-Acetamido-2-fluorobenzaldehyde 20 then is reacted with thiosemicarbazide to form 4-acetamido-2-fluorobenzaldehyde thiosemicarbazone 17 in 45% yield. An exemplary scheme for this reaction is shown below.

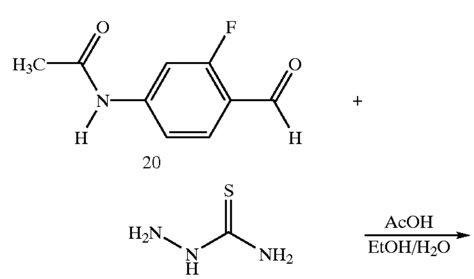

20

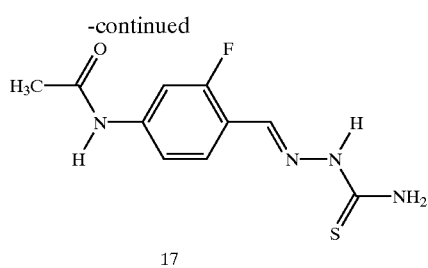

Synthesis of 4-acetamido-2-fluorobenzaldehyde thiosemicarbazone 17

Chloro derivative of Thiacetazone:

Chlorination of 4-acetamidobenzaldehyde 14 using NaOCl as a chlorinating reagent results in the chloro derivative 4-acetamido-3-chlorobenzaldehyde 24, as illustrated below.

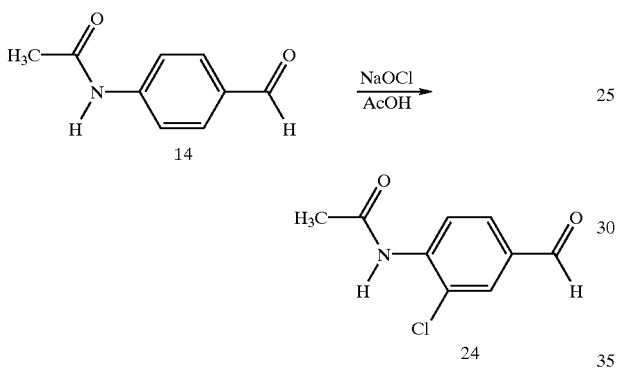

Preparation of 4-acetamido-3-chlorobenzaldehyde 24

The reaction of 4-acetamido-3-chlorobenzaldehyde 24 with thiosemicarbazide, shown below, forms thiosemicarbazone 25 in 90% yield.

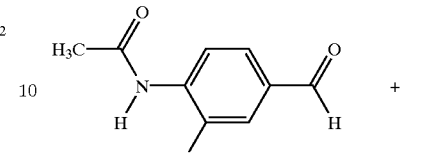

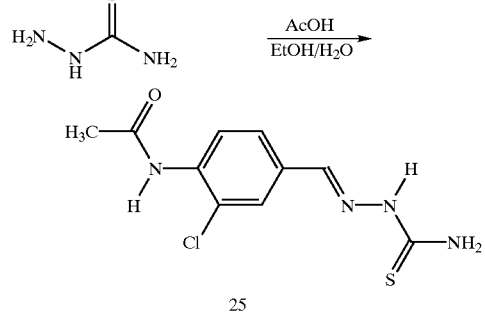

Synthesis of 4-acetamido-3-chlorobenzaldehyde thiosemicarbazone 25

Bromo derivative of Thiacetazone

Bromination of 4-acetamidobenzaldehyde 14 with $Br_2$/AcOH results in a solid mixture of three compounds, as detected by GC-MS (gas chromatograph-mass spectrometer). The three compounds are 4-acetamido-3-bromobenzaldehyde 26, 4-bromoacetanilide 27, and 2,4-dibromoacetanilide 28, as shown below.

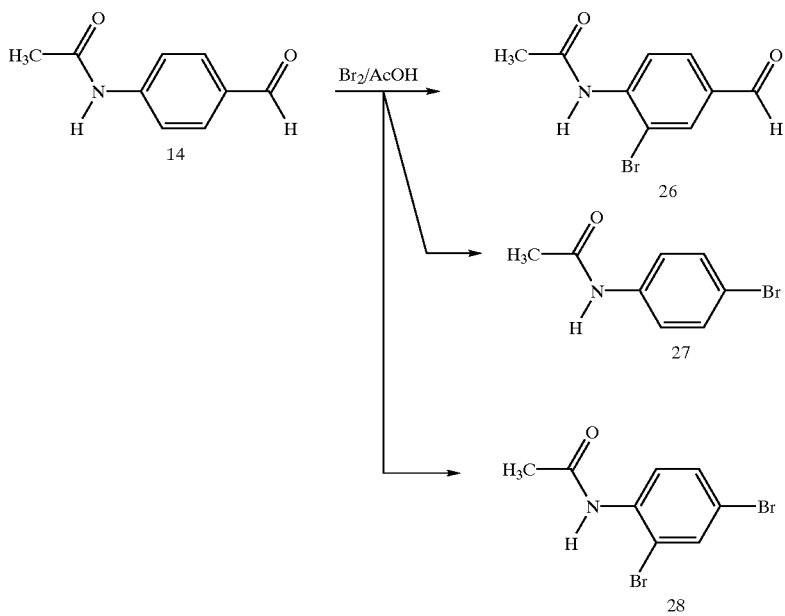

Bromination of 4-acetamidobenzaldehyde

Compound 26, 4-acetamido-3-bromobenzaldehyde, contains a formyl group, and reacts with thiosemicarbazide to produce 4-acetamido-3-bromobenzaldehyde thiosemicarbazone 29 as shown below.

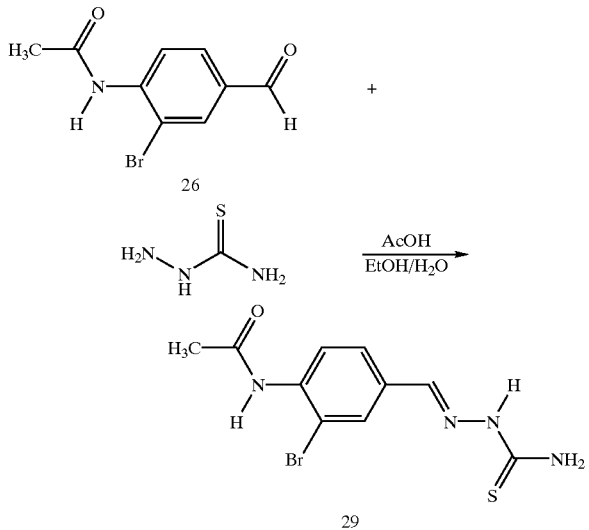

Synthesis of 4-acetamido-3-bromobenzaldehyde thiosemicarbazone 29

Iodo derivative of Thiacetazone

Iodination of 4-aminobenzonitrile 30 with ICl produces 4-amino-3-iodobenzonitrile 31. Acetylatation of 4-amino-3-iodobenzonitrile 31 results in compound 32, which can be reduced with Raney nickel to form 4-acetamido-3-iodobenzaldehyde 33. Reaction of compound 33 with thiosemicarbazide yields 4-acetamido-3-iodobenzaldehyde thiosemicarbazone 34, as illustrated below.

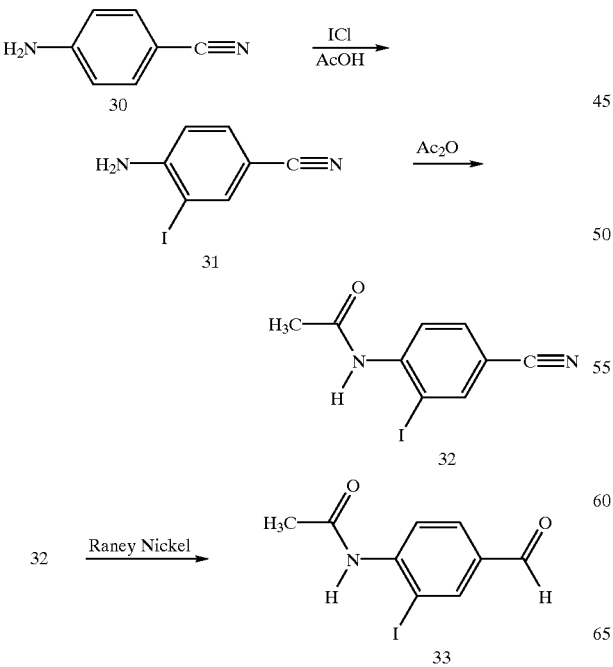

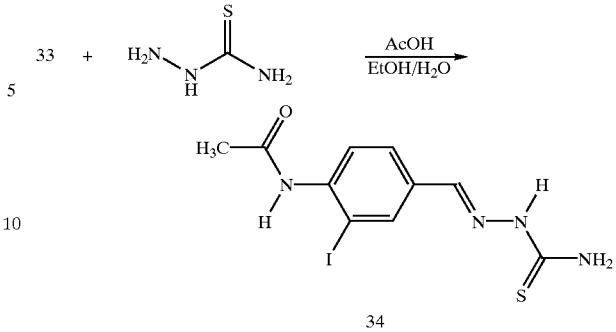

Synthesis of 4-acetamido-3-iodobenzaldehyde thiosemicarbazone 34

Conventional p-Aminosalicylic Acid p-Aminosalicylic Acid (identified hereinafter as PAS) 7 is an anti tuberculosis agent, however PAS has little effect on the respiration of *M. tuberculosis*. PAS is only effective against growing bacilli and the anti-tuberculosis activity of PAS is reversed with p-aminobenzoic acid. These indications suggest that PAS has a mechanism of action similar to that of sulfonamides.

In previous attempts, PAS has not been successfully modified into an anti- tuberculosis agent. Unless the PAS molecule is readily regenerated, modification to the structure of PAS typically results in loss of activity. Such modifications include: 1) primary amino group replacement with hydroxy, alkoxy, tertiary amines, or amides; 2) masking the hydroxyl group as an ether or ester; 3) replacing the hydroxyl group with a thiol or an amino group; 4) converting the carboxylic acid group to alkyl esters, amidines, amides, or nitrates.

Synthesis of fluorinated analog of p-Aminosalicylic Acid

Methyl 4-acetamidosalicylate 10, may be synthesized from PAS. This protected form of PAS, may be formed via esterification of the carboxylic acid group, followed by acetylation of the amine group, as shown below.

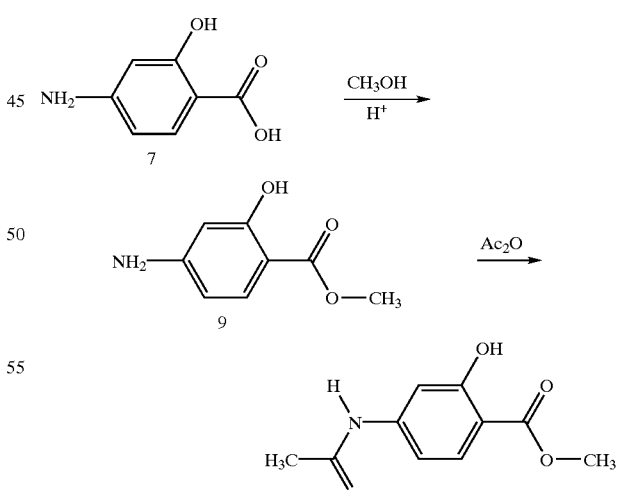

Preparation of methyl 4-acetamidosalicylate 10

Methyl 4-acetamidosalicylate 10 may be reacted with 1.5 equimoles of Selectfluor™, yielding a product characterized as 4-acetamido-5-fluorosalicylic acid methyl ester 11, as illustrated below.

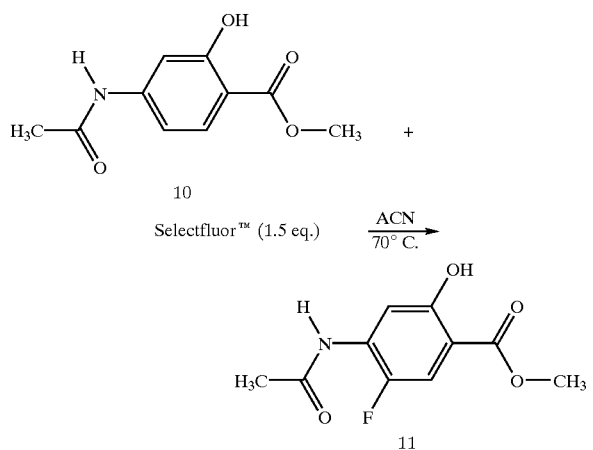

Synthesis of methyl 4-acetamido-5-fluorosalicylate 11

Hydrolysis of methyl 4-acetamido-5-fluorosalicylate 11 in 10% sodium hydroxide yields compound 12, as shown below.

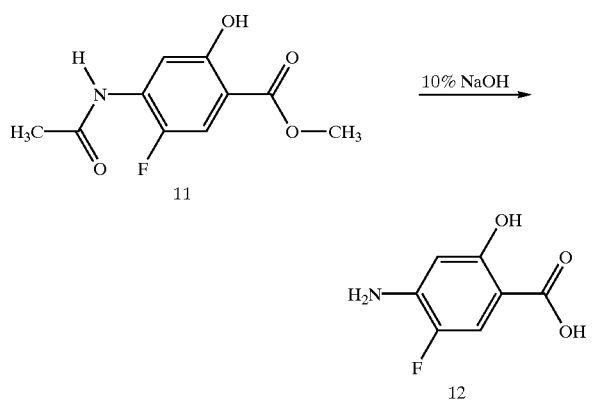

Preparation of 4-amino-5-fluorosalicylic acid 12

Evaluation of Anti-mycobacterial Activity

Testing and analysis of the halogenated compounds of the present invention were conducted using standard practices administered through the TAACF (Tuberculosis Antimicrobial Acquisition & Coordinating Facillity). The program is coordinated under the direction of the U. S. National Institute of Allergy and Infectious Diseases (NIAID), Southern Research Institute.

Pharmaceutical Compositions

The pharmaceutical composition of this invention comprises a halogenated compound and a pharmaceutically acceptable binder, wherein the halogenated compound is the halogenated thioacetazone previously described, the halogenated p-aminosalicylic acid previously described; or a combination thereof. The halogenated compound of this composition is an active ingredient in the composition having anti-mycobacterium activity, and may be used with one or more other conventional anti-mycobacterium agents such as isoniazid, rifampin, ethambutol and streptomycin. As used herein the term "pharmaceutically acceptable binder" is intended to have the conventional meaning of a non-toxic inert substance combined with the active ingredient for preparing an agreeable or convenient dosage form (i.e., an excipient). The pharmaceutical compositions containing the halogenated compound of this invention, is characterized by being active against at least one of the following Mycobacteria: *Mycobacterium tuberculosis* $H_{37}R_v$, *Mycobacterium tuberculosis* Erdman, *Mycobacterium avium* (American Type Culture Collection [ATCC] 25291), isoniazid-resistant *Mycobacterium tuberculosis* (ATCC 35822), rifampin-resistant *Mycobacterium tuberculosis* (ATCC 35838), ethambutol-resistant *Mycobacterium tuberculosis*, kanamycin-resistant *Mycobacterium tuberculosis*, ciprofloxacin-resistant *Mycobacterium tuberculosis* or a combination thereof.

The pharmaceutical compositions containing the halogenated compound of this invention, may be in a form suitable for oral use, for example as tablets, aqueous or oily suspensions, dispersible powders or granules, emulsions, hard or soft capsules. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Various pharmaceutically acceptable binders or excipients useful in the present invention are disclosed in columns 4–6 of U.S. Pat. No. 4,962,111, the disclosure of which is incorporated herein by reference.

The pharmaceutical compositions of this invention are particularly useful for treating a mammal infected with a Mycobacterium, by administering to the mammal a non-toxic, effective amount of a composition comprising the halogenated thioacetazone, the halogenated p-aminosalicylic acid of this invention, or a combination thereof; and a pharmaceutically acceptable binder. The compositions are particularly useful in treating a mammal infected with *Mycobacterium tuberculosis*.

Methods of In Vitro Evaluation of Anti-mycobacterial Activity

Primary screening of anti-mycobacterial activity was conducted at 6.25 μg/mL (or molar equivalent of highest molecular weight compound in a series of congeners) against *Mycobacterium tuberculosis* $H_{37}R_v$ (ATCC 27294) in BACTEC™ 12B medium using a broth microdilution assay. Specifically, the Microplate Alamar Blue Assay (hereinafter "MABA") was used. Compounds exhibiting fluorescence were tested in the BACTEC™ 460 radiometric system.

Some of the compounds demonstrating at least 90% inhibition in the primary screen were retested at lower concentrations against *M. tuberculosis* $H_{37}Rv$ to determine the actual minimum inhibitory concentration (hereinafter "MIC") using MABA. The MIC is defined as the lowest concentration effecting a reduction in fluorescence of 90% relative to controls.

Concurrent with the determination of MICs, compounds were tested for cytotoxicity ($1C_{50}$) in VERO cells at concentrations ≤62.5 μg/mL or 10× the MIC for *M. tuberculosis* $H_{37}Rv$ (when solubility in media permitted). After 72 hours exposure, viability was assessed on the basis of cellular conversion of MTT into a formazan product using the Promega CellTiter 96 Non-radioactive Cell Proliferation Assay Compounds for which the selectivity index, Si (i.e., 1 $C_{50}$:MIC ratio), was greater than 10 had in vitro activity confirmed by the BACTEC™ 460 radiometric system at 6.25 µg/mL. Compounds were then tested for killing of *M. tuberculosis* Erdman (ATCC 35801) in monolayers of mouse bone marrow macrophages. Compounds were tested at 4-fold concentrations equivalent to 0.25, 1, 4, and 16× the MIC. The test measured $EC_{90}$ and $EC_{99}$ values, which are the lowest concentration effecting a 90% and 99% reduction, respectively, in colony forming units at seven days as compared to drug-free controls.

Concurrent with the testing of compounds in macrophages, MICs were determined in a MABA against a strain of *M. avium* (ATCC 25291) and against three strains of singly-drug-resistant (SDR) *M. tuberculosis*. Each SDR strain is resistant to a single anti-tuberculosis drug). Compounds were tested against *M. tuberculosis* strains resistant to isoniazid (ATTC 35822), rifampin (ATCC 35838), and one additional SDR strain chosen on the basis of compound type (thiacetazone-resistant *M. tuberculosis* in the case of structure I and PAS-resistant *M. tuberculosis* in the case of structure IV). Confirmatory testing also occurred against drug-sensitive *M. tuberculosis* strains $H_{37}Rv$ and Erdman. The minimum bactericidal concentration (MBC) was then determined for *M. tuberculosis* $H_{37}Rv$ and Erdman (and for the appropriate drug-resistant strain, for analogs of known anti-tubercular drugs) by subculturing onto drug-free solid media and enumerating colony forming units following exposure in supplemented Middlebrook 7H9 media to drug concentrations equivalent to and higher than the previously determined MICs of the respective strains.

Tuberculosis Animal Model

Compounds were tested for their capacity to inhibit the growth of virulent *M. tuberculosis* in a realistic in vivo aerosol mouse model. Mice were exposed to an aerosol of *M. tuberculosis* Erdman, which deposits approximately 50 bacilli into the lungs of the animal. The course of the infection is then followed in the lungs and spleen for 50 days by plating homogenates of harvested organs [n=5] on nutrient agar and determining bacterial numbers. As the growing infection was slowly controlled and contained, a peak number of about log 5.0 was observed in the infected lungs.

Test compounds were administered to groups of mice starting on day 20 post-inoculation. Three dose levels of drug were given (generally intraperitoneal) once per day, or oral gavage twice per day); an additional group was given isoniazid as a positive control. Bacterial numbers were assessed on days 35 and 50, and compared to untreated control values. The data are expressed as the $\log_{10}$ protection provided by a given dose of the compound against the growth of the organism in the untreated control group. Statistical tests are also applied to the raw data to determine levels of significance. For new compound classes it may be necessary to determine a minimum toxic dose (MTD) before running the animal model.

Evaluation of Anti-*M. avium* Activity

Higher level evaluation of compounds against *M. avium* is available for compounds showing an *M. avium* MIC ≤6.25 μg/mL. Expanded primary screening was conducted at a range of 1 μg/mL–64 μg/mL against five *M. avium* clinical isolates (strains 100, 101, 108, 109, 116) in Middlebrook 7H9 broth using a MABA and a BACTEC 460 system.

Compounds with MIC≤8 μg/mL in at least three of the five strains tested were retested at lower concentrations against 30 strains, including five strains resistant to clanthromycin (MIC>32 μg/mL). Compounds that demonstrated significant activity against the panel of 30 strains were tested against three *M. avium* strains (100, 101, 109) representing the three serotypes encountered in AIDS patients (8, 1, 4, respectively). This test measures intracellular activity of the compound in an infected macrophage model using the human monocyte cell line U937. Potential synergism with ethambutol is examined by adding ethambutol (4 μ/mL) to the compound.

In vivo activity was studied in a mouse model for *M. avium* infection. Beige-C57BL/J bg female mice were infected I.V.(intravenous) with $3\times10^7$ cfu of bacilli. After one week, therapy was initiated and continued for four weeks. The liver and spleen were aseptically dissected, weighed, and homogenized. Serial dilutions of the liver and spleen tissues were plated onto 7H1 1 agar for quantitative culture.

The synthesis and test results of this invention will now be illustrated by the following examples but is not intended to be limited thereby.

EXAMPLE 1

Synthesis of 4-Acetamido-3-fluorobenzaldehyde (15)

A solution of 20.56 g (0.058 mole) Selectfluor™ (Aldrich 43,947-9) in 400 mL acetonitrile (Fisher 996-4) was obtained by heating the mixture at 70–800. To this solution was added 4.73g (0.029 mole) 4-acetamidobenzaldehyde (14) (Aldrich, Al 80-0) and the mixture was heated at 700 under reflux for 72 hours. The reaction mixture was allowed to cool and then added into 500 mL diethyl ether. The mixture was washed first with 3×300 mL water and then with 300 mL of saturated solution of sodium bicarbonate, dried over anhydrous $MgSO_4$ and evaporated to give 2.4 g (45%) of yellow solid, which was recrystallized from water containing 1 g activated charcoal (Darco S51) to yield 0.91g (19%) of 15 as pale yellow crystals, mp 131–133° (ref. 133–135°). Infrared (IR) and NMR analysis gave the following results: IR (potassium bromide): 3256 (NH), 1674 (C=O),1609,1535, 1431, 1257 $cm^{-1}$. $^1H$ nmr (90 MHz, DMSO-$d_6$):δ10.10 (1 H, br s, NH), 9.9 (1H; d, $^4J$=2 Hz; formyl H), 8.36 (1H; t, J=8 Hz; H-5), 7.81–7.70 (2H, m, H-2 and H-6 ), 2.17 (3H, s, $CH_3$).

EXAMPLE 2

Synthesis of 4-Acetamido-3-fluorobenzaldehyde thiosemicarbazone (16)

A solution of 0.18 g (0.002 mole) thiosemicarbazide (Aldrich T3,340-5) in 6 mL water containing 0.4 ml acetic acid was added to a solution of 0.36 g (0.002 mole) 4-acetamido-3-fluorobenzaldehyde (15) in 5 mL ethanol at 70°. The mixture was stirred at this temperature for 30 minutes. A white precipitate developed in the solution, which was filtered after cooling the reaction mixture to give 0.45 g (90%) of white powder, mp 230–233° (decomposed). This compound was crystallized from ethanol twice, yielding 0.1 7 g of 16 as white crystals, mp 231° (dec.). Infrared (IR) and NMR analysis gave the following results: IR (potassium bromide): 3358, 3293, 3167, 1666 (C=O),1581, 1518, 1286 $cm^1$. $^1H$ nmr (90 MHz, DMSO-$d_6$):δ11.49 (1H, s, thiosemicarbazone NH), 9.86 (1 H, s, amide NH), 8.22–7.40 (5H, m, aromatic Hs and $NH_2$), 2.13 (3H, s, $CH_3$). Elemental analysis was calculated for the structures in the examples provided herein using ChemWindows™ Software (available through BioRad) and results are given in percent weight. Anal.: Calcd. for $C_{10}H_{11}FN_40S$ (254.28): C, 47.23; H, 4.36; F, 7.47; N, 22.03; S, 12.61. Found: C, 47.25; H, 4.53; F, 6.89; N, 22.07; S, 12.30.

EXAMPLE 3

Synthesis of 4-Acetamido-2-fluorobenzaldehyde thiosemicarbazone (17)

A solution of 0.182 g (0.002 mole) of thiosemicarbazide (Aldrich T3,340-5) in 6 mL of water containing 0.4 mL of acetic acid was added to a solution of 0.36 g (0.002 mole) 4-acetamido-3-fluorobenzaldehyde (20) in 5 mL of ethanol at 70°. The mixture was stirred at this temperature for 30 minutes. A white precipitate developed in the reaction mixture, which was filtered after cooling down to give 0.22 g (44% crude) of white powder which was recrystallized from methanol and dried, yielding 0.12 g (24%) of 17 as white crystals, mp 232–235° (dec.). Infrared (IR) and NMR analysis gave the following results: IR (potassium bromide): 3441, 3317, 3167,1673 (C=O), 1600, 1534,1415 $cm^1$. $^1H$ nmr (90 MHz, DMSO-$d_6$):δ 11.53 (1H, s, thiosemicarbazone NH), 10.35 (1H, s, amide NH), 8.25 (1H, s, imine H), 8.08 (1H; t, $^3J_{H5\text{-}H6}$=9Hz, $^4J_{F\text{-}H6}$=9 Hz; H-6), 8.04 (2H; br s; thiosemicarbazone $NH_2$), 7.7 (1H, dd, $^3J_{F\text{-}H3}$=12.6 Hz, $^4J_{H5\text{-}H3}$=1.8 Hz; H-3), 7.27 (1H; dd, $^3J_{H6\text{-}H5}$=9 Hz, $^4J_{H3\text{-}H5}$= 1.8 Hz; H-5), 2.11 (3H, s, $CH_3$). Anal. Calcd. for $C_{10}H_{11}FN_4OS$ (254.28): C, 47.23; H, 4.36; F, 7.47; N, 22.03; S, 12.61. Found: C, 46.88; H, 4.35; F, 7.30; N, 21.62; S, 12.11.

EXAMPLE 4
Synthesis of 3-Fluoro-4-iodoacetanilide (23)
A solution of 1 mL concentrated sulfuric acid and 6.7 mL water in 33.5 mL glacial acetic acid was added to a mixture of 5.15 g (0.0336 mole) 3'-fluoroacetanilide (22) (Aldrich 36,378-2), 1.52 g (0.0072 mole) periodic acid dihydrate (Fisher A-223) and 3.4g (0.0134 mole) iodine (Fisher 137-500). The resulting purple solution was heated at 70° under reflux for 2 hours (until the purple color turned to a strong orange color). The reaction mixture was poured into 85 mL of water, and it was stirred until all the sticky material turned to solid. The solid was filtered (1.58 g, 17%) and recrystallized from water containing 0.5 g activated charcoal (Darco S51) to give 0.93 g (10%) of 23 as white crystals, mp 153–155°. Infrared (IR) and NMR analysis gave the following results: IR (potassium bromide): 3310 (NH), 1672 (C=O),1603, 1535, 1410 $cm^{-3}$. $^1H$ nmr (90 MHz, DMSO-$d_6$):δ 10.26 (1H, s, NH), 7.84–7.63 (2H, m, H-2 and H-5), 7.16 (1H; dd, $^3J_{H5\text{-}H6}$=9 Hz, $^4J_{H2\text{-}H6}$=2.2 Hz; H-6).

EXAMPLE 5
Synthesis of 4-Acetamido-2-fluorobenzonitrile (21) A mixture of 2.79 g (0.01 mole) of 3-fluoro-4-iodoacetanilide (23) and 0.98 g (0.011 mole) copper(1) cyanide (J. T. Baker Chemical 1870) in 5 mL dry N-methyl pyrrolidinone (Aldrich 32,863-4) under nitrogen was heated at 2000 for 20 hours. The resulting dark mixture was poured, while still hot, into a warm solution of 1.92 g of sodium cyanide (Aldrich 38,097-0) in 6.5-mL of water, with vigorous stirring. The mixture was extracted with 3×20 mL of dichloromethane and the organic layer was washed first with 30 ml Of 10% sodium hydroxide and then with 30 mL of water. After being dried over anhydrous sodium sulfate, the solvent was evaporated to a brown-black liquid, which gave some crystals upon remaining in the lab overnight. The solid was filtered, rinsed with absolute ethanol and recrystallized from ethanol/water to give 0.9 g (50%) of 21 as off-white crystals, mp 190–192°. Infrared (IR) and NMR analysis gave the following results: IR (potassium bromide): 3317 (NH), 2228 (CN), 1682 (C=O),1601, 1530, 1421, 1250 $cm^{-1}$. $^1H$ nmr (90 MHz, DMSO-$d_6$):δ 10.62 (1H, br s, NH), 7.93–7.50 (2H, m, H-3 and H-6), 7.43 (1 H; dd, $^3J_{H6\text{-}H5}$=8.7 Hz, $^4J_{H3\text{-}H5}$=1.9 Hz; H-5), 2.13 (3H, s, $CH_3$).

EXAMPLE 6
Synthesis of 4-Acetamido-2-fluorobenzaldehyde (20)
A mixture of 1.17 g (0.0066 mole) of 4-acetamido-2-fluorobenzonitrile (21) and 1.2 g of Raney nickel (Aldrich, 22,167-8, activated according to the method explained in Vogel's Textbook of Practical Organic Chemistry) in 18 mL of 75% formic acid (Aldrich 10,652-6) was heated under reflux at 80–90° for one hour. The reaction mixture was allowed to cool and filtered using a filter aid. The residue on the filter aid was rinsed with 2×5 mL of absolute ethanol and the combined filtrates were evaporated to give 1.41 g of a yellow solid which was dissolved in acetone. The residual undissolved solid was filtered and the filtrate was evaporated and washed with cold methanol to give 0.94 g (78%) of 20 as yellow powder, mp 157–160°. Infrared (IR) and NMR analysis gave the following results: IR (potassium bromide): 3279 (NH), 1690 (C=O),1611, 1510, 1400, 1269 $cm^1$. $^1H$ nmr (90 MHz, DMSO-$d_6$):δ 10.58 (1H, br s, NH), 10.10 (1H, s, formyl H), 7.80 (1H; t, $^3J_{H5\text{-}H6}$=8.4 Hz, $^4J_{F\text{-}H6}$=8.4 Hz; H-6), 7.77 (1H; dd, $^3J_{F\text{-}H}$=13.7 Hz, $^4J_{H5\text{-}H3}$=1.9 Hz; H-3), 7.40 (1H; dd, $^3J_{H6\text{-}H5}$=8.4 Hz, $^4J_{H3\text{-}H5}$=1.9 Hz; H-5), 2.12 (3H, s, $CH_3$).

EXAMPLE 7
Synthesis of 4-Acetamido-3-chlorobenzaldehyde (24) To a solution of 6.43 g (0.039 mole) 4-acetamidobenzaldehyde (14) (Aldrich, A180-0) in 55 mL of glacial acetic acid, was added 100 mL of 5.25% solution of sodium hypochlorite (Clorox, Pathmark brand) and the reaction mixture was stirred at room temperature for 48 hours. A white precipitate developed in the reaction mixture when a sample of the reaction mixture was taken off for TLC. The mixture was poured into 100 mL water and filtered to give 2.5 g (32%) of 24 as white powder, mp 110–113°. Infrared (IR) and NMR analysis gave the following results: IR (potassium bromide): 3334 (NH), 1706 (C=O),1688 (C=O), 1575, 1527, 1375 $cm^{-1.}$ $^1H$ nmr (90 MHz, DMSO-$d_6$): 89.95 (lH, s, formyl H), 9.74 (1H, brs, NH), 8.21 (1H; d, $^3J_{H6\text{-}H5}$=9.0 Hz; H-5), 8.02 (1H; d, $^4J_{H6\text{-}H2}$=1.8 Hz; H-2), 7.87 (1H; dd, $^3J_{H5\text{-}H6}$=9.0 Hz, $^4J_{H2\text{-}H6}$=1.8 Hz; H-6), 2.22 (3H, s, $CH_3$).

EXAMPLE 8
Synthesis of 4-Acetamido-3-chlorobenzaldehyde thiosemicarbazone (25)
A solution of 0.73 g (0.008 mole) of thiosemicarbazide (Aldrich T3,340-5) in 24 mL of water containing 1.6 mL of glacial acetic acid was added to a solution of 1.58 g of (0.008 mole) 4-acetamido-3-chlorobenzaldehyde (24) in 20 mL of ethanol at 70°. The mixture was stirred at this temperature for 45 minutes. A white precipitate developed in the reaction mixture, which was filtered after cooling to give 1.95 g (90%) of 25 as off white crystals, mp 235–2380°. Infrared (IR) and NMR analysis gave the following results: IR (potassium bromide): 3423, 3260, 3132, 1701 (C=O), 1594, 1508, 1303 $cm^{-1}$. $^1H$ nmr (90 MHz, DMSO-$d_6$):δ 11.47 (1 H, s, thiosemicarbazone NH), 9.35 (1 H, s, amide NH), 8.15–7.91 (5H; m; H-2, H-5, imine H and thiosemicarbazone $NH_2$), 7.6 (1H; dd, $^3J_{H5\text{-}H6}$=8.1 Hz, $^4J_{H2\text{-}H6}$=1.8 Hz; H-6) 2.18 (3H, s, $CH_3$). Anal. Calcd. for $C_{10}H_{11}ClN_4OS$ (270.73): C, 44.36; H, 4.10; Cl, 13.10; N, 20.69; S, 11.84. Found: C, 44.51; H, 4.14; Cl, 12.91; N, 20.67; S, 12.27.

EXAMPLE 9
Synthesis of 4-Acetamido-3-bromobenzaldehyde thiosemicarbazone (29)
A solution of 1.32 mL (4.25 g, 0.0265 mole) of bromine (Aldrich 20,788-8) in 6.25 mL of glacial acetic acid was added to a solution of 4.07 g (0.025 mole) of 4-acetamidobenzaldehyde (14) in 22 mL glacial acetic acid slowly at room temperature. A precipitate developed in the reaction mixture when almost half of the bromine solution was added. The mixture was stirred at room temperature for one hour further and then poured into 100 mL of water. The mixture was stirred for 30 minutes untill the strong yellow color of the solution was gone. The precipitate was filtered and dried to give 1.2 g of a yellow powder. Conducting a GC-MS on this compound showed three major peaks, one of them being compound 26 and the other two were characterized as 4-bromoacetanilide (27) and 2,4-dibromoacetanilide (28). Several recrystallization from methanol did not yield a pure compound. To a solution of 0.48 g of this mixture in 5 mL of ethanol, was added a solution of 0.182 g (0.002 mole) of thiosemicarbazide (Aldrich T3,340-5) in 6 mL of water containing 0.4 mL of acetic acid at 700. The mixture was stirred at this temperature for 45 minutes. A white precipitate developed in the reaction mixture, which was filtered without cooling the mixture to give 0.2 g of white crystals of 29, mp 232–2350. Infrared (IR) and NMR analysis gave the following results: IR (potassium bromide): 3418, 3235, 3146, 1690 (C=O), 1598, 1520, 1299 cm$^1$. $^1$H nmr (90 MHz, DMSO-d$_6$):δ 11.50 (IH, s, thiosemicarbazone NH), 9.47 (1H, s, amide NH), 8.25–7.72 (6H; m; aromatic Hs, imine H and thiosemicarbazone NH$_2$), 2.12 (3H, s, CH$_3$).

AnaL Calcd. for $C_{10}H_{11}BrN_4OS$ (315.18): C, 38.1 1; H, 3.52; Br, 25.35; N, 17.78; S, 10.17. Found: C, 38.58; H, 3.74; Br, 24.98; N, 17.94; S, 11.52.

EXAMPLE 10
Synthesis of 4-Amino-3-iodobenzonitrile (31)

To a solution of 5.9 g (0.05 mole) of 4-aminobenzonitrile (30) (Aldrich 14,775-3) in 25 mL of glacial acetic acid was added dropwise a solution of 8.12 g (0.05 mole) of iodine monochloride (Aldrich 20,822-1) in 5 mL of glacial acetic acid. During the addition, the temperature rose to 40°. The solution was stirred at room temperature for 20 minutes. A solid developed in the reaction mixture and the deep brown color of the solution started fading gradually. The mixture was poured into 250 mL of water and stirred for 10 minutes to give a pale brown solid which was filtered and recrystallized from methanol/water containing one gram of activated charcoal (Darco S51) yielding 9.3 g (76%) of white crystals of 31, mp 110–112°. Infrared (IR) and NMR analysis gave the following results: IR (potassium bromide): 3454 and 3346 (NH$_2$), 2214 (CN), 1621, 1496 cm$^1$. $^1$H nmr (90 MHz, CDCl$_3$):δ 7.91 (1H; d, $^4$J$_{H6-H2}$=1.8 Hz; H-2), 7.41 (1H; dd, $^3$J$_{H5-H6}$=8.4, $^4$J$_{H2-H6}$=1.8 Hz; H-6), 6.73 (1 H; d, $^3$J$_{H6-H5}$=8.4 Hz, H-5), 4.67 (2H, br s, NH$_2$).

EXAMPLE 11
Synthesis of 4-Acetamido-3-iodobenzonitrile (32)

A mixture of 8.54 g (0.035 mole) of 4-amino-3-iodobenzonitrile (31), 16 mL (16.32 g, 0.16 mole) of acetic anhydride and five drops of concentrated sulfuric acid was heated at 700 under reflux for 10 minutes (the mixture became thick when the temperature reached 400 and some manual stirring was required). The reaction mixture was poured over 400 mL of cold water and stirred for 5 minutes to give a white solid which was filtered and dried, yielding 9.48 g (95%) of 32 as white powder, mp 176–181°. Infrared (IR) and NMR analysis gave the following results: IR (potassium bromide): 3276 (NH), 2230 (CN), 1663 (C=O), 1517, 1297 cm$^{-1}$. $^1$H nmr (90 MHz, CDCl$_3$):δ 8.73 (1H, br s, NH), 8.13-8.05 (2H, m, H-5 and H-2), 7.65 (1 H; dd, $^3$J$_{H5-H6}$=8.4 Hz, $^4$J$_{H2-H6}$=1.8 Hz; H-6), 2.25 (3H, s, CH$_3$).

EXAMPLE 12
Synthesis of 4-Acetamido-3-iodobenzaldehyde (33)

A mixture of 5.64 g (0.0197 mole) of 4-acetamido-3-iodobenzonitrile (32), 3.6 g of Raney nickel (Aldrich 22,167-8, activated according to the method explained in Vogels Textbook of Practical Organic Chemistry) and 55 ml of 75% formic acid (Aldrich 10,652-6) was heated under reflux at 85° for 1.5 hours. While the reaction mixture was still hot, it was filtered through a cake of filter aid and the residue was washed with 3×10 mL of absolute ethanol. The solvent was evaporated to give 4.69 (82%) of a yellow-green solid which was crystallized from methanol/water, yielding 4.2 g (73%) of white crystals of 33, mp 145–147°. Infrared (IR) and NMR analysis gave the following results: IR (potassium bromide): 3272 (NH), 1700 (C=O), 1661 (C=O), 1565, 1524, 1368, 1198 cm$^{-1}$. $^1$H nmr (90 MHz, CDCl$_3$):δ 9.86 (1H, S, formyl H), 8.51 (1H; d, $^3$J$_{H6-H5}$=8.6 HZ; H-5), 8.31 (1H; d, $^4$J$_{H6-H2}$=1.8 Hz, H-2), 7.85 (1H; dd, $^3$J$_{H5-H6}$=8.6 Hz, $^4$J$_{H2-H6}$=1.8 Hz), 7.7 (1H, br S, NH), 2.3 (3H, S, CH$_3$).

EXAMPLE 13
Synthesis of 4-Acetamido-3-iodobenzaldehyde thiosemicarbazone (34) A solution of 0.728 g (0.008 mole) of thiosemicarbazide (Aldrich T3,340-5) in 25 mL of water containing 1.6 mL of glacial acetic acid was added to a solution of 2.31 g (0.008 mole) of 4-acetamido-3-iodobenzaldehyde (33) in 40 mL of absolute ethanol (heating was required to make this dissolve) at 80°. The mixture was stirred at this temperature for 45 minutes. A white precipitate developed in the solution which was filtered after cooling the reaction mixture to give 2.55 (88%) of 34 as white crystals, mp 241–43° (dec.). Infrared (IR) and NMR analysis gave the following results: IR (potassium bromide): 3382, 3242, 3153, 1694 (C=O), 1592, 1502, 1296 cm$^{-1}$. $^1$H nmr (90 MHz, DMSO-d$_6$):δ 11.5 (1 H, s, thiosemicarbazone NH), 9.42 (1 H, s, amide NH), 8.43 (1 H; d, J$_{H2-H6}$=1.7 Hz; H-2), 8.2 (2H, br s, thiosemicarbazone NH$_2$), 8.0 (1H. , imine H), 7.76 (1H; dd, $^3$J$_{H5-H6}$=8.5 Hz,$^4$J$_{H2-H6}$=1.7 Hz; H-6), 7.52 (1 H; d,$^3$J$_{H6-H5}$=8.5 Hz; H-5), 2.1 (3H, s, CH$_3$). Anal. Calcd. for $C_{10}H_{11}IN_4OS$ (315.18): C, 33.16; H, 3.06; I, 35.04; N, 15.47; S, 8.85. Found: C, 33.29; H, 3.18; I, 35.09; N, 15.35; S, 9.30.

EXAMPLE 14
Synthesis of Methyl 4-aminosalicylate (9)

To a suspension of 9.18 g (0.06 mole) 4-aminosalicylic acid (7) (Aldrich A7,960-4) in 40 mL of dry methanol was added 8 mL of concentrated sulfuric acid slowly. The mixture was heated under reflux at 70 ° C. for 1.5 hours and then it was cooled in an ice-water bath. Enough concentrated ammonium hydroxide solution was added to adjust the pH to 9 and the precipitate was filtered, rinsed with water and dried to give 6.01 g (60%) of 9 as a solid, mp 118–120° (ref. 120–121°). Infrared (IR) and NMR analysis gave the following results: IR (potassium bromide): 3473 and 3379 (NH$_2$), 1643 (C=O),1284, cm$^{-1}$. $^1$H nmr (90 MHz, CDCl$_3$):δ 10.96 (1H, s, OH), 7.6 (1H; d, $^3$J$_{H5-H6}$=9 Hz; H-6), 6.20–6.08 (2H, cm, H-3 and H-5), 4.2 (2H; br s; NH$_2$), 3.87 (3H, s, CH$_3$).

EXAMPLE 15
Synthesis of Methyl 4-acetamidosalicylate (10)

To a suspension of 4.17 g (0.025 mole) methyl 4-aminosalicylate (9) in 20 mL water, was added 3 mL (0.032 mole) acetic anhydride (Aldrich 11,004-3) while stirring. The mixture was heated at 800 for 30 minutes and cooled to room temperature. The precipitate was collected and added into 100 ml of 10% hydrochloric acid. This suspension was stirred at room temperature for 10 minutes, filtered and dried to give 4.3 g (82%) of a crude solid, which was recrystallized from H$_2$O/CH$_3$OH, yielding 3 g (70%) of 10 as white crystals, mp 153–154 . Infrared (IR) and NMR analysis gave the following results: IR (potassium bromide): 3319(NH), 1680 (C=O),1604, 1157 cm$^{-1}$. $^1$H nmr (90 MHz, CDCl$_3$ +DMSO-d$_6$):δ 10.80 (1H, S, OH), 9.74 (1H, br s, NH), 7.73 (1H; d, $^3$J$_{H5-H6}$=9 Hz; H-6), 7.37 (1H; d, $^4$J$_{H5-H3}$=1.8 Hz; H-3),7.11 (1H; dd, $^3$J$_{H6-H5}$=9HZ, $^4$J$_{H3-H5}$=1.8 Hz; H-5), 3.91 (3H; s; OCH$_3$), 2.15 (3H, s, CH$_3$).

EXAMPLE 16
Synthesis of Methyl 4-acetamido-5-fluorosalicylate (11)

A solution of 10.62g (0.03 mole) Selectfluor™ (Aldrich 43,947-9) in 200 mL acetonitrile (Fisher A996-4) was obtained by heating the mixture at 70–80°. Then 4.1 8 g (0.2 mole) methyl 4-acetamidosalicylate (10) was added and the solution was heated under reflux for 4.5 hours at 80°. The reaction mixture was allowed to cool down and added into 350 mL of diethyl ether. The mixture was washed first with 4×250 ml water and then with 150 ml saturated solution of sodium bicarbonate, dried over anhydrous magnesium sulfate and evaporated, yielding 2 g (44%) of off-white solid, which was recrystallized from methanol twice to give 1 g (22%) of 11 as white crystals, mp 169–172.5°. Infrared (IR) and NMR analysis gave the following results: IR (potassium bromide): 3294 (NH), 1681 (C=O),1630 (C=O), 1547, 1260, 1185 cm$^{-1}$. $^1$H nmr (90 MHz, CDCl$_3$ +DMSO-d$_6$):δ 10.56 (1H, s, OH), 9.86 (1H, br s, NH), 7.96 (1 H; d, $^4J_{F-H3}$=7.2 Hz; H-3), 7.49 (1 H; d, $^3J_{F-H6}$=11.70 Hz; H-6), 3.93 (3H; s; OCH$_3$), 2.22 (3H, s, CH$_3$). Anal. Calcd. for C$_{10}$H$_{10}$FNO$_4$ (227.19): C, 52.87; H, 4.44; F, 8.36; N, 6.17. Found: C, 52.86; H, 4.43; F, 7.89; N, 6.17.

EXAMPLE 17
Synthesis of 4-Amino-5-fluorosalicylic Acid (12)

A solution of 1 g (0.0047 mole) methyl 4-acetamido-5-fluorosalicylate (11) in 20 mL of 20% sodium hydroxide solution was heated under reflux for 2 hours and was cooled. Enough concentrated hydrochloric acid was added to bring the pH to 2. The precipitate was filtered and dried to yield 0.54 g (72%) of white powder, which was recrystalized from water/methanol, giving 12 as white crystals, mp 171–172°. Infrared (IR) and NMR analysis gave the following results: IR (potassium bromide): 3486 & 3380 (NH$_2$), 1656 (C=O), 1535,1446 cm$^{-1}$. $^1$H nmr (90 MHz, Acetone-d$_6$):δ 10.99 (2H, very b s, OH and COOH), 7.40 (1H; d, $^3J_{F-H6}$=11.7 Hz; H-6), 6.33 (1 H; d,$^4J_{F-H3}$=7.2 Hz; H-3), 5.74 (2H, br s, NH$_2$). Anal. Calcd. for C$_7$H$_6$FNO$_3$ (171.12): C, 49.13; H, 3.53; F, 11.10; N, 8.18. Found: C, 48.91; H, 3.62; F, 11.12; N, 8.03.

EXAMPLE 18
Anti-*M. tuberculosis* activity of 3-fluoro analog of Thiacetazone

TABLE 1

Results of preliminary anti-TB tests on 4-acetamido-3-fluorobenzaldehyde thiosemicarbazone 16

| Sample ID | Structure | Assay | MIC ug/ml | % inhibition | Activity |
|---|---|---|---|---|---|
| Compound 16 | (structure) | Bactec | <12.5 | 99 | Positive |

Table 1 shows primary screening test results for 4-acetamido-3- fluorobenzaldehyde thiosemicarbazone 16. The compound displayed 99% inhibition of tuberculosis under primary screening conditions.

Since 16 had demonstrated >90% inhibition in the primary screening, it was tested at lower concentrations against *M. tuberculosis* H$_{37}$Rv (in MABA system) to determine its actual Minimum Inhibitory Concentration (MIC). The compound was also tested for overt toxicity (IC$_{50}$). The results are presented in Table 2:

TABLE 2

Minimum Inhibitory Concentration (MIC) and Overt Toxicity (IC$_{50}$) of Compound 16

| Sample ID | Structure | Assay | MIC ug/ml | % inh. | IC50 ug/ml | SI | Comments |
|---|---|---|---|---|---|---|---|
| Comp. 16 | (structure) | Alamar | 0.2 | 99 | >62.5 | >312.5 | MIC of rifampicin = 0.015 ug/ml; IC50 of INH = 601.6; IC50 of rifampicin = 77.7 |

The selectivity index (SI) is defined as the ratio of the measured IC$_{50}$ in VERO cells to the MIC (IC$_{50}$: MIC). 4-acetamido-3-fluorobenzaldehyde thiosemicarbazone 16 showed MIC =0.2 μg/ml and SI >312.5, and thus qualified for additional screening tests under the protocol of the TAACF. The compound was tested for efficacy in vitro in a TB-infected macrophage model (results in Table 3). The MICs of the compound were determined against drug-sensitive *M. tuberculosis* strains H$_{37}$Rv, Erdman, and TB strains resistant to isoniazid (INH), rifampin (RMP), ethambutol HCl (EMB), kanamycin sulfate (KM) and ciprofloxacin (CIP). The results are shown in Table 4:

TABLE 3

Effective Concentrations (EC$_{90}$ and EC$_{99}$) for 16 against *M. tuberculosis* Erdman in monolayers of mouse bone marrow macrophage

| Sample ID | Structure | MIC (ug/ml) | SI | EC90 | EC99 | EC90/MIC |
|---|---|---|---|---|---|---|
| Comp. 16 | 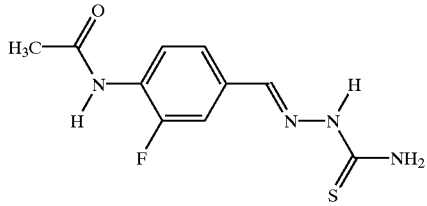 | 0.2 | >312.5 | 1.7 | >3.2 | 8.5 |

TABLE 4

MICs of 16 against *M. tuberculosis* H$_{37}$Rv, Erdman and drug-resistant strains

| Sample ID | Structure | Assay | MIC H37Rv (ug/ml) | MIC Erdman (ug/ml) | MIC INH-R (ug/ml) | MIC RMP-R (ug/ml) | MIC EMB-R (ug/ml) | MIC KM-R (ug/ml) | MIC CIP-R (ug/ml) |
|---|---|---|---|---|---|---|---|---|---|
| Comp. 16 | 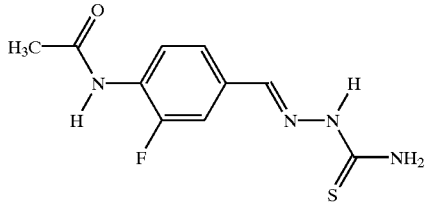 | Alamar | <=0.1 | 0.2 | <=0.1 | <=0.1 | 0.2 | <=0.1 | <=0.1 |

Cross resistance data is shown in Table 5 and is measured as a ratio of the MIC for specific single-drug resistant strains (Table 4) versus the MIC against drug sensitive strains (Table 2). A large ratio suggests that the compound does not target the resistant strain, and indicates that the compound has the same mechanism of action that the resistant strain circumvents.

The ratios in Table 5 indicate no cross-resistance between 16 and isoniazid, rifampin, ethambutol, kanamycin or ciprofloxacin. The minimum bactericidal concentration (MBC) was determined for *M. tuberculosis* H$_{37}$Rv, RMP-resistant and INH-resistant. Results are shown in Table 6:

TABLE 5

Ratio of MIC in drug-resistant strains versus MIC in drug-sensitive strain

| Sample ID | Structure | INH-R/L2 MIC | RMP-R/L2 MIC | EMB-R/L2 MIC | KM-R/L2 MIC | CIP-R/L2 MIC |
|---|---|---|---|---|---|---|
| Comp. 16 | 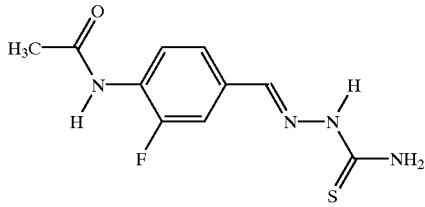 | <=0.5 | <=0.5 | 1 | <=0.5 | <=0.5 |

TABLE 6

Minimum bactericidal concentrations (MBCs) of 16 against H₃₇Rv and drug-resistant strains

| Sample ID | Structure | Assay | MIC H37Rv (ug/ml) | H37Rv MBC | H37Rv MBC/MIC | RMP-R MBC | RMP-R MBC/MIC | INH-R MBC | INH-R MBC/MIC |
|---|---|---|---|---|---|---|---|---|---|
| Comp. 16 | [structure: acetamido-fluoro-benzylidene thiosemicarbazone] | Alamar | <=0.1 | 6.25 | >62.5 | >6.25 | >62.5 | >6.25 | >62.5 |

The MIC of thiacetazone against *M. tuberculosis* $H_{37}Rv$ (determined by MABA system) is >2.0 µg/ml. The MIC value of 16 is ≤0.1 µg/ml, suggesting that compound 16 is about 20 times more effective against Tuberculosis than the current anti-tuberculosis agent.

EXAMPLE 19

Anti-*M. tuberculosis* activity of the 2-flouro-, 3-chloro-, 3-bromo- and 3-iodo-analogs of thiacetazone Table7 shows the primary screening test results for the 2-flouro-, 3-chloro-, 3-bromo- and 3-iodo- derivatives of thiacetazone:

TABLE 7

Results of preliminary anti-TB tests on compound 17, 25, 29 and 34

| Sample ID | Structure | Assay | MIC ug/ml | % inhibition | Activity |
|---|---|---|---|---|---|
| Compound 17 | [structure with F substituent] | Bactec | <6.25 | 94 | Positive |
| Compound 25 | [structure with Cl substituent] | Bactec | <6.25 | 92 | Positive |
| Compound 29 | [structure with Br substituent] | Bactec | <6.25 | 93 | Positive |
| Compound 34 | [structure with I substituent] | Bactec | <6.25 | 93 | Positive |

All of the halogenated compounds 17, 25, 29 and 34 had the lowest minimum inhibitory concentration measurable by the primary screening test, and greater than 90% inhibition. Thus, they are all strong candidates for effective therapeutic agents.

EXAMPLE 20

Anti-*M. tuberculosis* activity of the 5-flouro- analog of p-Aminosalicylic Acid Table 8 shows the results of the preliminary screening tests of the prodrug, compound 11 and the fluorinated analog of PAS, 4-Amino-5-fluorosalicylic Acid 12.

The selectivity index (SI) is defined as the ratio of the measured $IC_{50}$ in VERO cells to the MIC. 4-Amino-5-fluorosalicylic Acid 12 showed 6.25 μg/ml and SI>10, and thus qualified for additional screening tests under the protocol of the TAACF. The compound was tested for efficacy in vitro in a *M. tuberculosis* infected macrophage model (results in Table 9). The MICs of the compound were determined against drug-sensitive *M. tuberculosis* strains $H_{37}Rv$, Erdman, and TB strains resistant to isoniazid (INH), rifampin (RMP), ethambutol HCI (EMB), kanamycin sulfate (KM) and ciprofloxacin (CIP). The results are shown in Table 10.

TABLE 8

Results of preliminary anti-TB tests on compound 12 and 11

| Sample ID | Structure | Assay | MIC ug/ml | % inhibition | Activity |
| --- | --- | --- | --- | --- | --- |
| Compound 12 | 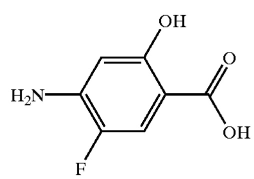 | Bactec | <12.5 | 94 | Positive |
| Compound 11 | 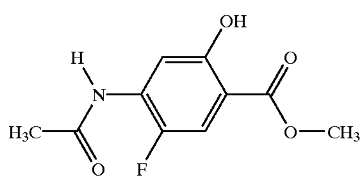 | Bactec | >12.5 | 0 | Negative |

The results in table 8 show that 4-Amino-5-fluorosalicylic Acid 12 demonstrated >90% inhibition in the primary screening. The actual MIC for 12 was determined in Microplate Alamar Blue Assay (MABA). Concurrent with the determination of MICs, the compound was tested for overt cytotoxicity ($IC_{50}$) in VERO cells. The results of these tests are presented in Table 9:

TABLE 9

MIC and $IC_{50}$ of 4-Amino-5-fluorosalicylic Acid 12

| Sample ID | Structure | Assay | MIC ug/ml | % inh. | IC50 ug/ml | SI | Comments |
| --- | --- | --- | --- | --- | --- | --- | --- |
| Compound 12 | 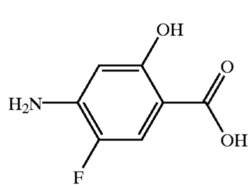 | Alamar | 6.25 | 94 | >62.5 | >10 | MIC of rifampicin = 0.015 ug/ml<br>IC50 of INH = 601.6<br>IC50 of rifampicin = 77.7 |

TABLE 10

MICs of 12 against *M. tuberculosis* $H_{37}RV$, Erdman and drug-resistant strains

| Sample ID | Structure | Assay | MIC H37Rv (ug/ml) | MIC Erdman (ug/ml) | MIC INH-R (ug/ml) | MIC RMP-R (ug/ml) | MIC EMB-R (ug/ml) | MIC KM-R (ug/ml) | MIC CIP-R (ug/ml) |
|---|---|---|---|---|---|---|---|---|---|
| Comp. 12 | H₂N–C₆H₂(OH)(F)–COOH | Alamar | <=3.13 | 12.5 | 25 | 6.25 | <=3.13 | 6.25 | 6.25 |

Cross resistance data is shown in Table 11 and is measured as a ratio of the MIC for specific single-drug resistant strains (Table 10) versus the MIC against drug sensitive strains (Table 9). A large ratio suggests that the compound does not target the resistant strain, and indicates that the compound has the same mechanism of action that the resistant strain circumvents.

MIC of p-aminosalicylic acid (PAS) against *M. tuberculosis* $H_{37}Rv$ (determined by MABA system) is 1.25 μg/ml. The MIC for 4-Amino-5-fluorosalicylic Acid 12 is ≤3.13. This indicates that 12 is an anti-tuberculosis agent.

Those skilled in the art having the benefit of the teachings of the present invention as hereinabove set forth, can effect numerous modifications thereto. These modifications are to be construed as being encompassed within the scope of the present invention as set forth in the appended claims.

TABLE 11

The ratios of MIC in drug-resistant strains versus MIC in drug-sensitive strain

| Sample ID | Structure | INH-R/L2 MIC | PMR-R/L2 MIC | EMB-R/L2 MIC | KM-R/L2 MIC | CIP-R/L2 MIC |
|---|---|---|---|---|---|---|
| Comp. 12 | H₂N–C₆H₂(OH)(F)–COOH | 4 | 1 | <=0.50 | 1 | 1 |

The minimal bactericidal concentration (MBC) was determined for *M. tuberculosis* $H_{37}Rv$, RMP-resistant and INH-resistant. Results are presented in Table 12:

TABLE 12

Minimum bactericidal concentrations (MBCs) of 4-Amino-5-fluorosalicylic Acid 12 against $H_{37}Rv$ and drug-resistant strains

| Sample ID | Structure | Assay | MIC H37Rv (ug/ml) | H37Rv MBC | H37Rv MBC/MIC | RMP-R MBC | RMP-R MBC/MIC | INH-R MBC | INH-R MBC/MIC |
|---|---|---|---|---|---|---|---|---|---|
| Comp. 12 | H₂N–C₆H₂(OH)(F)–COOH | Alamar | <=3.13 | >200 | >64 | >200 | >63.9 | >200 | >63.9 |

What is claimed is:

1. A halogenated compound having Structure I or a pharmaceutically acceptable salt thereof:

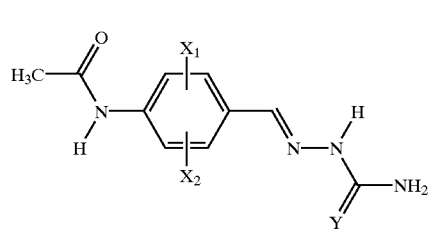

Structure I wherein $X_1$ is a halogen and $X_2$ is a second halogen or hydrogen, and Y is sulfur or oxygen, wherein $X_1$ is fluorine.

2. The halogenated compound of claim 1 wherein X2 is fluorine.

3. The halogenated compound of claim 1 wherein $X_2$ is hydrogen.

4. The compound of claim 1 wherein $X_2$ is selected from the group consisting of bromine, iodine and chlorine.

5. The halogenated compound of claim 1 which is a pharmaceutically acceptable salt thereof.

6. The halogenated compound of claim 1 wherein Y is sulfur.

7. A composition comprising the halogenated compound of claim 1 and a pharmaceutically acceptable binder, wherein the halogenated compound has anti-mycobacterium activity.

8. The composition of claim 7 wherein the anti-mycobacterium activity is being active against *Mycobacterium tuberculosis* $H_{37}$Rv, *Mycobacterium tuberculosis* Erdman, *Mycobacterium tuberculosis* avium (ATCC 25291), isoniazid-resistant *Mycobacterium tuberculosis* (ATTC 35822), rifampin-resistant *Mycobacterium tuberculosis* (ATCC 35838), ethambutol-resistant *Mycobacterium tuberculosis*, kanamycin-resistant *Mycobacterium tuberculosis*, ciprofloxacin-resistant *Mycobacterium tuberculosis*, or a combination thereof.

9. The composition of claim 7 wherein the halogenated compound has anti-*Mycobacterium tuberculosis* activity.

10. A halogenated compound having Structure II:

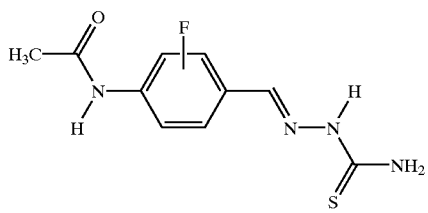

Structure II or a pharmaceutically acceptable salt thereof.

11. A composition comprising a halogenated compound of claim 10 or a pharmaceutically acceptable salt thereof and a pharmaceutically acceptable binder, wherein the halogenated compound has anti-mycobacterium activity.

12. The composition of claim 11 wherein the halogenated compound has anti-*Mycobacterium tuberculosis* activity.

13. A halogenated compound having Structure I or a pharmaceutically acceptable salt thereof:

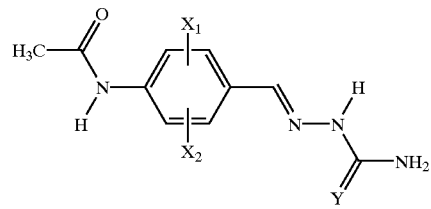

Structure I wherein $X_1$ and $X_2$ are the same halogen, and Y is sulfur or oxygen.

14. A method of treating a mammal infected with a mycobacterium, comprising administering to the mammal a non-toxic, effective amount of a composition comprising the halogenated compound of claim 1 and a pharmaceutically acceptable binder, wherein the halogenated compound has anti-mycobacterium activity.

15. The method of claim 14 wherein the mycobacterium is *Mycobacterium tuberculosis*.

16. The method of claim 14 wherein the mycobacterium is *Mycobacterium tuberculosis* $H_{37}$Rv, *Mycobacterium tuberculosis* Erdman, *Mycobacterium tuberculosis* avium (ATCC 25291), isoniazid-resistant *Mycobacterium tuberculosis* (ATTC 35822), rifampin-resistant *Mycobacterium tuberculosis* (ATCC 35838), ethambutol-resistant *Mycobacterium tuberculosis*, kanamycin-resistant *Mycobacterium tuberculosis*, ciprofloxacin-resistant *Mycobacterium tuberculosis*, or a combination thereof.

17. A method of treating a mammal infected with a mycobacterium, comprising administering to the mammal a non-toxic, effective amount of a composition comprising a halogenated compound of claim 10 or a pharmaceutically acceptable salt thereof and a pharmaceutically acceptable binder, wherein the halogenated compound has anti-mycobacterium activity.

18. The method of claim 4 wherein the mycobacterium is *Mycobacterium tuberculosis*.

19. A method of treating a mammal infected with a mycobacterium, comprising administering to the mammal a non-toxic, effective amount of a composition comprising the halogenated compound of claim 13 and a pharmaceutically acceptable binder, wherein the halogenated compound has anti-mycobacterium activity.

20. The method of claim wherein the mycobacterium is *Mycobacterium tuberculosis*.

21. The method of claim 19 wherein the Mycobacterium is *Mycobacterium tuberculosis* $H_{37}$Rv, *Mycobacterium tuberculosis* Erdman, *Mycobacterium tuberculosis* avium (ATCC 25291), isoniazid-resistant *Mycobacterium tuberculosis* (ATTC 35822), rifampin-resistant *Mycobacterium tuberculosis* (ATCC 35838), ethambutol-resistant *Mycobacterium tuberculosis*, kanamycin-resistant *Mycobacterium tuberculosis*, ciprofloxacin-resistant *Mycobacterium tuberculosis*, or a combination thereof.

* * * * *

UNITED STATES PATENT AND TRADEMARK OFFICE
CERTIFICATE OF CORRECTION

PATENT NO. : 6,482,982 B1  Page 1 of 1
DATED : November 19, 2002
INVENTOR(S) : Kobarfard et al.

It is certified that error appears in the above-identified patent and that said Letters Patent is hereby corrected as shown below:

Column 30,
Lines 5-13, delete " 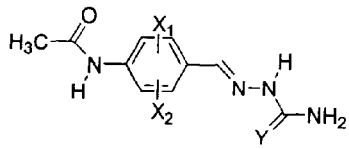 " and insert therefore -- 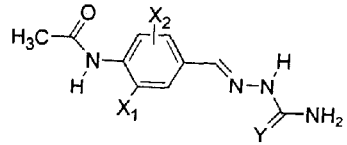 --

Line 41, delete "claim 4" and insert therefore -- claim 17 --;
Line 49, after the word "claim" and before the word "wherein" insert -- 19 --.

Signed and Sealed this

Thirteenth Day of May, 2003

JAMES E. ROGAN
*Director of the United States Patent and Trademark Office*